United States Patent [19]

Slack

[11] Patent Number: 5,440,003

[45] Date of Patent: * Aug. 8, 1995

[54] LIQUID METHYLENE DIPHENYL DIISOCYANATE

[75] Inventor: William E. Slack, Moundsville, W. Va.

[73] Assignee: Miles Inc., Pittsburgh, Pa.

[*] Notice: The portion of the term of this patent subsequent to Jun. 7, 2011 has been disclaimed.

[21] Appl. No.: 116,183

[22] Filed: Sep. 2, 1993

[51] Int. Cl.⁶ ............................................... C08G 18/72
[52] U.S. Cl. ........................................ 528/48; 528/45; 528/49; 528/55; 528/67; 252/182.22; 560/27
[58] Field of Search .................. 528/48, 45, 49, 55, 528/67; 252/182.22; 560/27

[56] References Cited

U.S. PATENT DOCUMENTS

| | | |
|---|---|---|
| 3,644,457 | 2/1972 | König et al. . |
| 4,055,548 | 10/1977 | Carleton et al. . |
| 4,115,429 | 9/1978 | Reiff et al. . |
| 4,118,411 | 10/1978 | Reiff et al. . |
| 4,160,080 | 7/1979 | König et al. ............... 528/59 |
| 4,261,852 | 4/1981 | Carroll et al. ............... 528/59 |
| 4,490,300 | 12/1984 | Allen et al. ................. 521/155 |
| 4,738,991 | 4/1988 | Narayan ..................... 521/124 |
| 4,866,103 | 9/1989 | Cassidy et al. ............. 521/159 |
| 4,910,333 | 3/1990 | Slack ......................... 560/351 |
| 5,319,054 | 6/1994 | Slack et al. ................. 528/48 |

FOREIGN PATENT DOCUMENTS 7199176 12/1971 Japan .

*Primary Examiner*—Joseph L. Schofer
*Assistant Examiner*—John M. Cooney, Jr.
*Attorney, Agent, or Firm*—Joseph C. Gil; Godfried R. Akorli; Lyndanne M. Whalen

[57] ABSTRACT

Disclosed herein are processes for the production of allophanate-modified diphenylmethane diisocyanate prepolymers and the products produced by the processes which are both stable and liquid at 25° C. by reacting (i) 4,4'-diphenyl-methane diisocyanate containing from 2 to 60% by weight 2,4'-MDI and less than 6% by weight of the 2,2'-MDI with (ii) an aromatic alcohol containing between 6 and 18 carbon atoms such as phenol, with the resulting product being converted to the allophanate having an isocyanate group content of from 12 to 32% by weight.

7 Claims, No Drawings

1

LIQUID METHYLENE DIPHENYL DIISOCYANATE

BACKGROUND OF THE INVENTION

1. Field of the Invention

The present invention relates to liquid methylene diphenyl diisocyanates. More specifically, the present invention relates to aromatic alcohol-based, allophanate-modified methylene diphenyl diisocyanates and prepolymers made with them.

2. Brief Description of the Prior Art

Liquid methylene diphenyl diisocyanates are generally known in the art. U.S. Pat. No. 3,644,457 discloses room-temperature stable liquid isocyanates derived from one mole of diphenylmethane diisocyanate and 0.1 to 0.3 mols of poly-1,2-propylene ether glycol.

U.S. Pat. No. 4,055,548 discloses liquid isocyanate prepolymer compositions obtained by reacting polymethylene polyphenylisocyanate containing from about 65 to 85 percent by weight of methylene bis(phenyl)isocyanate with a polyoxyethylene glycol having molecular weight of from 200 to 600 in an equivalent ratio 0.0185–0.15:1.

U.S. Pat. No. 4,115,429 and 4,118,411 disclose low temperature (as low as −5 degrees Centigrade) storage stable liquid diphenylmethane diisocyanates which are produced by reacting diphenylmethane diisocyanates having a specified 2,4-isomer content with propylene glycol or poly-1,2-propylene ether glycol.

U.S. Pat. No. 4,261,852 discloses liquid polyisocyanate compositions comprising (a) the reaction product of 90 to 50% by weight of a reaction product of diphenylmethane diisocyanate and a polyoxypropylene diol or triol having hydroxyl equivalent weight of from 750 to 3000, said reaction product having NCO content of from 8 to 26% by weight, and (B) from about 10 to 50% by weight of a diphenylmethane diisocyanate containing from 30 to 65% by weight of diphenylmethane diisocyanate, the remainder being polymethylene polyphenyl polyisocyanate.

U.S. Pat. No. 4,490,300 discloses room temperature stable liquid isocyanates which are derived by reacting diphenylmethane diisocyanate with an aliphatic diol having a pendant aromatic group, e.g., 2-methyl-2-phenyl-1,3-propanediol or phenyl-1-2-ethanediol.

U.S. Pat. No. 4,490,300 discloses room temperature stable liquid isocyanates which are derived by reacting diphenylmethane diisocyanate with monoallylether of trimethylolpropane.

U.S. Pat. No. 4,738,991 discloses organic polyisocyanates characterized by allophanate linkages which are prepared by reacting an organic polyisocyanate including 2,4- and 4,4-methylenediphenyl diisocyanate with poly or monohydric alcohol in the presence of an organo metallic catalyst. The catalyst is then deactivated using a compound such as an inorganic acid, organic acid, organic chloroformate or an organic acid chloride.

U.S. Pat. No. 4,866,103 discloses a polyisocyanate composition for use in producing elastomers in a RIM process, said composition being the product of reacting an alcohol and/or thiol having an average functionality of from about 1.5 to about 4 and an average equivalent weight of at least 500 with at least 2 equivalents per hydroxyl and/or thiol equivalent of an organic polyisocyanate including 4,4- and 2,4-isomers of diphenylmethane diisocyanate under such conditions that at least about 20% of the initially formed urethane and/or thiourethane groups are converted to allophanate and/or thioallophanate groups.

Other prior art relating to the preparation of allophanates which contain isocyanates is British Patent 994,890 which relates to the reaction of urethane isocyanates with excess diisocyanate either by heat alone or in the presence of a catalyst such as a metal carboxylate, a metal chelate or a tertiary amine, until the isocyanate content is reduced to that which is obtained theoretically when the complete reaction of the urethane groups is achieved.

U.S. Pat. No. 4,160,080 discloses a process for producing allophanate containing aliphatically and/or cycloaliphatically bound isocyanate groups in which compounds containing urethane groups are reacted with polyisocyanates having aliphatic and/or cycloaliphatic isocyanate groups in the presence of a strong acid. The process is generally conducted at a temperature of from 90° C. to 140° C. for about 4 to 20 hours.

Japanese Patent Application No. 1971-99176 discloses a method of preparing liquid diphenylmethane diisocyanate by reacting diphenylmethane diisocyanate with aliphatic monovalent alcohol.

By the present invention there is provided a novel liquid isocyanate.

SUMMARY OF THE INVENTION

In accordance with the foregoing, the present invention in the first embodiment encompasses a process for the production of a prepolymer containing an allophanate-modified MDI which is stable and liquid at 25° C., by reacting (i) 4,4'-diphenylmethane diisocyanate containing from 2 to 60% by weight 2,4'-MDI and less than 6% by weight of the 2,2'-MDI with (ii) an aromatic alcohol containing between 6 and 18 carbon atoms with the resulting product being converted to an allophanate-modified MDI having an isocyanate group content of about 12 to 32% by weight.

In the second embodiment of the invention, the process further comprises reacting the allophanate-modified MDI such as described above with an organic material containing two or more hydroxyl, primary amine or secondary amine groups or any combination thereof to produce a prepolymer containing an allophanate modified MDI having an isocyanate content of about 5 to 30 percent.

The allophanate-modified MDI prepolymers obtained by the above processes are also encompassed by the claimed invention.

In accordance with process of the invention, the allophanate-modified MDI can be prepared by reacting the afore-described specified isomer composition of the diphenylmethane diisocyanate with an aromatic alcohol, at about 40° C. to about 115° C. to produce a urethane product, followed by converting the resultant urethane to the allophanate-modified MDI at 60°–110° C., using zinc acetylacetonate as catalyst, and benzoyl chloride as a stopper for the catalyst, in a 2:1 weight ratio of benzoyl chloride to zinc acetylacetonate.

It is a distinct feature of the invention that the prepolymers containing the allophanate-modified MDI are stable and liquid at 25° C. By the term "stable" herein is meant that the prepolymer has less than 1% absolute change in the % NCO and less than 10% change in the viscosity when stored at 25° C. for 3 months. By the term "liquid" herein is meant that the prepolymer does not precipitate solids when stored at 25° C. for 3 months.

The liquid isocyanate prepolymers of the invention have been found to be particularly useful in automotive RIM, shoe soles and rigid foam applications.

DETAILED DESCRIPTION OF THE INVENTION

In the first embodiment, the prepolymer containing the allophanate-modified MDI is stable and liquid at 25 degrees Centigrade and has an isocyanate content of about 12 to 32 percent and preferably 20 to 30 percent. In the second embodiment, the prepolymer containing the allophanate-modified MDI is also stable and liquid at 25 degrees Centigrade and has an isocyanate content of 5 to 30 and preferably 12 to 23 percent.

As set forth above, the diphenylmethane diisocyanate employed herein comprises 4,4'-diphenylmethane diisocyanate containing about 2 to 60% and preferably 2 to 20% by weight 2,4'-diphenylmethane diisocyanate, and less than 6% and preferably about 0 to 0.7% by weight of the 2,2'-diphenylmethane diisocyanate.

Aromatic alcohols are those alcohols having the alcoholic hydroxyl group attached to the aromatic group. Specific examples of the aromatic alcohols can be phenol, 1-naphthol, 2-naphthol, m-cresol, o-chlorophenol, p-bromophenol, m-nitrophenol and o-fluorophenol.

In the process for the production of the allophanate-modified MDI wherein a urethane is first prepared, the diphenylmethane diisocyanate and the aromatic alcohol can be reacted at a temperature of 40 to 90 and typically at 60° C., followed by the addition of a an allophanate-forming catalyst to the resulting urethane, at 60° to 120° C., in order to form the allophanate.

Alternately, an allophanate-forming catalyst, and the aromatic alcohol can be added together to the methylene diphenyl diisocyanate at 40°–60° C., followed by heating the resulting mixture at about 60 to 120 and typically at 90° C. to form the allophanate.

The catalyst in the resultant product is typically neutralized before the reaction with organic materials containing hydroxyl groups or amine groups as described hereinafter. As such the catalysts useful herein are those that can be neutralized or otherwise stopped from adversely affecting subsequent reactions.

Examples of the catalyst can be zinc acetylacetonate which is preferred, zinc 2-ethylhexanoate, cobalt 2-ethylhexanoate, cobalt naphthenate, lead linoresinate. Examples of the catalyst stopper can be acidic materials such as anhydrous hydrochloric acid, sulfuric acid, bis(2-ethylhexyl)hydrogen phosphate, benzoyl chloride, Lewis acids and the like, in the ratio of 2 equivalents of the acid to each mole of the catalyst. Solvents which are typically inert to the isocyanate, for example toluene, tetrahydrofuran or o-dichloro-benzene can be employed.

In the second embodiment of the invention, the process for the production of the prepolymer containing the allophanate-modified MDI further to the process steps as described above comprises the step of reacting the allophanate-modified MDI having an isocyanate group content of from 12.0 to 32% with an isocyanate reactive material comprising an organic material having two or more and preferably 2 to 3 isocyanate reactive groups such as hydroxyl groups, primary or secondary amine groups or any combination thereof.

Generally, the subject urethane, urea or biuret reaction is carried out in a manner which is well known in the polyurethane chemistry by, say, heating the reactants to a temperature of from about 40 to 150 and preferably 50 to 100 degrees Centigrade to form the urethane or urea and at 100° to 150° C. and preferably 110° to 120° C. to form the biuret.

The organic compounds containing at least two isocyanate-reactive groups can be divided into two groups, i.e., high molecular weight compounds with molecular weights from 400 to about 6,000, preferably from 2000 to about 5,000, and low molecular weight compounds with molecular weights below 400 and preferably about 60 to 200. The molecular weights are number average molecular weights ($M_n$) and are determined by end group analysis (OH number). Examples of the high molecular weight compounds are amine-terminated polyethers, amine-terminated polyesters, polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and amine-terminated polyethers and polyesters are preferred. The resultant isocyanate prepolymer has an isocyanate group content of from 5 to 30% and preferably 12 to 23% by weight.

Suitable polyester polyols include reaction products of polyhydric, preferably dihydric alcohols to which trihydric alcohols may be added and polybasic, preferably dibasic carboxylic acids. Instead of these polycarboxylic acids, the corresponding carboxylic acid anhydrides or polycarboxylic acid esters of lower alcohols or mixtures thereof may be used for preparing the polyesters. The polycarboxylic acids may be aliphatic, cycloaliphatic, aromatic and/or heterocyclic and they may be substituted, e.g. by halogen atoms, and/or unsaturated. The following are mentioned as examples: succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride, endomethylene tetrahydrophthalic acid anhydride; glutaric acid anhydride; maleic acid; maleic acid anhydride; fumaric acid; dimeric and trimeric fatty acids such as oleic acid, which may be mixed with monomeric fatty acids; dimethyl terephthalates and bis-glycol terephthalate. Suitable polyhydric alcohols include, e.g. ethylene glycol; propylene glycol-(1,2) and -(1,3); butylene glycol-(1,4) and -(1,3); hexanediol-(1,6); octanediol-(1,8); neopentyl glycol; cyclohexanedimethanol (1,4-bis-hydroxymethylcyclohexane); 2-methyl-1,3-propanediol; 2,2,4-trimethyl-1,3-pentanediol; triethylene glycol; tetraethylene glycol; polyethylene glycol; dipropylene glycol; polypropylene glycol; dibutylene glycol and polybutylene glycol, glycerine and trimethlyolpropane. The polyesters may also contain a portion of carboxyl end groups. Polyesters of lactones, e.g. ε-caprolactone or hydroxycarboxylic acids, e.g. ω-hydroxycaproic acid, may also be used.

Polycarbonates containing hydroxyl groups include those known per se such as the products obtained from the reaction of diols such as propanediol-(1,3), butanediol-(1,4) and/or hexanediol-(1,6), diethylene glycol, triethylene glycol or tetraethylene glycol with phosgene, diarylcarbonates such as diphenylcarbonate or with cyclic carbonates such as ethylene or propylene carbonate. Also suitable are polyester carbonates obtained from the above-mentioned polyesters or polylactones with phosgene, diaryl carbonates or cyclic carbonates.

Suitable polyether polyols are obtained in known manner by the reaction of starting compounds which contain reactive hydrogen atoms with alkylene oxides such as ethylene oxide, propylene oxide, butylene oxide, styrene oxide, tetrahydrofuran, epichlorohydrin or mixtures of these alkylene oxides. It is preferred that the polyethers do not contain more than about 10% by weight of ethylene oxide units. Most preferably, polyethers obtained without the addition of ethylene oxide are used. Suitable starting compounds containing reactive hydrogen atoms include the polyhydric alcohols set forth for preparing the polyester polyols and, in addition, water, methanol, ethanol, 1,2,6-hexane triol, 1,2,4-butane triol, trimethylol ethane, pentaerythritol, mannitol, sorbitol, methyl glycoside, sucrose, phenol, isononyl phenol, resorcinol, hydroquinone, 1,1,1- or 1,1,2-tris-(hydroxylphenyl)-ethane.

Polyethers modified by vinyl polymers are also suitable for the process according to the invention. Products of this kind may be obtained by polymerizing, e.g. styrene and acrylonitrile in the presence of polyethers (U.S. Pat. Nos. 3,383,351; 3,304,273; 3,523,095; 3,110,695 and German Patent No. 1,152,536).

Among the polythioethers which should be particularly mentioned are the condensation products obtained from thiodiglycol on its own and/or with other glycols, dicarboxylic acids, formaldehyde, aminocarboxylic acids or amino alcohols. The products obtained are either polythio-mixed ethers, polythioether esters or polythioether ester amides, depending on the co-components.

Suitable amine-terminated polyethers can be prepared by reacting a primary amine with a polyether containing a terminal leaving group such as halides or mesylates as disclosed in commonly assigned U.S. patent application Ser. No. 07/957,929, filed on Oct. 7, 1992 or disclosed in U.S. Pat. Nos. 3,666,726, 3,691,112 and 5,066,824.

Suitable polyacetals include the compounds which can be prepared from aldehydes, e.g. formaldehyde, and glycols such as diethylene glycol, triethylene glycol, ethoxylated 4,4'-dihydroxy-diphenyldimethylmethane, and hexanediol-(1,6). Polyacetals suitable for the purpose of the invention may also be prepared by the polymerization of cyclic acetals.

Suitable polyhydroxy polyester amides and polyamines include the predominantly linear condensates obtained from polybasic saturated and unsaturated carboxylic acids or their anhydrides and polyvalent saturated or unsaturated aminoalcohols, diamines, polyamines and mixtures thereof.

Suitable monomers for producing hydroxy-functional polyacrylates include acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate and 2- isocyanatoethyl methacrylate.

The low molecular weight material containing two or more hydroxyl groups having an average molecular weight of 60 to 200 may be used in combination with or instead of the high molecular weight material containing two or more hydroxyl or amine groups. They include the polyhydric alcohols which have previously been described for the preparation of the polyester polyols and polyether polyols. Dihydric alcohols are preferred. The weight ratio of the low molecular weight material containing two or more hydroxyl groups to the high molecular weight material containing two or more hydroxyl or amine groups can be from 0.001 to 2 and preferably 0.01 to 0.40.

In addition to the above-mentioned components which are preferably difunctional, monofunctional and even small portions of trifunctional and higher functional components generally known in polyurethane chemistry, such as trimethylolpropane, may be used in special cases in which slight branching of the resultant product is desired.

Suitable amine-terminated polyethers and polyesters are compounds having molecular weights of about 400 to 6000 and having a functionality of two or more and preferably 2 to 3.

In the process of the invention, isocyanate reactive materials can be reacted with the allophanate-modified ethylene diphenyl diisocyanate over the temperature range of 40 to 150 and preferably 50° to 100° C., over a period of 0.1 to 2 hours. Catalysts and solvents can be employed to aid the reaction. Examples of the useful catalysts can be selected from the group consisting of di-n-butyltin dichloride, di-n-butyltin diacetate, di-n-butyltin dilaurate, triethylenediamine, and bismuth nitrate. Examples of the useful solvents can be selected from the group consisting of dioxane, chlorobenzene, toluene, and tetrahydrofuran.

The resultant product is a liquid isocyanate prepolymer which has been found to be particularly useful in the preparation of isocyanate reaction products such as polyurethanes.

The invention is further illustrated by the following non-limiting examples.

EXAMPLES

In the examples which follow, these materials were used:

Polyol A: a propylene glycol/propylene oxide adduct having a 2000 molecular weight.

Polyol B: a glycerine/propylene oxide/ethylene oxide adduct with the ethylene oxide being present as a 17% by weight termination having a 4800 molecular weight.

Polyol C: a glycerine/propylene oxide adduct having a 3000 molecular weight.

Polyol D: a glycerine/propylene oxide/ethylene oxide adduct with
the ethylene oxide being present as a 13% by weight termination nation having a 6000 molecular weight.

PG: 1,2-propylene glycol 1,3 XB: 1,3-butanediol

MDI-X: Diphenylmethane diisocyanate which contains less than 6% by weight 2,2'-MDI and in which X represents the percent by weight 2,4'-MDI with the remainder being the 4,4'- and 2,2'-isomers of MDI.

Isocyanate A: 150 parts of MDI-2 and 8.55 parts of phenol were charged to a stirred reactor and heated to 55° C. 0.016 part of zinc acetylacetonate was added and the stirred reaction mixture was heated to 90° C. After one hour at 90° C. the NCO content was 27.0%. The reaction mixture was cooled to 74° C. and 0.04 parts of benzoyl chloride was added. The reaction mixture was then cooled to about 25° C. and stored at about 25° C. until used.

Isocyanate B: 100 parts of MDI-2 and 3.9 parts of phenol were charged to a stirred reactor and heated to 60° C. After 50 minutes at 60° C., 0.012 part of zinc acetylacetonate was added and the reaction mixture was heated to 90° C. After 40 minutes at 90° C. the NCO content was 29.0%. The reaction mixture was cooled to 65° C. and 0.03 part benzoyl chloride was added. The reaction mixture was then cooled to about 40° C. and stored at about 40° C. until used.

Example 1

100 parts of Isocyanate B were charged to a reactor and heated to 60° C. 18.5 parts of Polyol A and 4 parts of 1,3 XB were added to the stirred isocyanate at such a rate that the temperature was maintained at 60° C. ±5° C. The reaction mixture was held at 60° C. for about 2 hours and then cooled to 25° C. The resultant product, which had an isocyanate group content of 19.9%, was a clear liquid and storage stable at 25° C.

Examples 2 through 14

Examples 2 through 14 used the process of Example 1. All the products were clear liquids and storage stable at 25° C. The materials used and the percent NCO results obtained are as set forth in the following table.

TABLE 1

| Example | Isocyanate Used | PBW Iso. | Polyol Used | PBW Polyol | Diol Used | PBW Diol | NCO Content % by wt. |
|---|---|---|---|---|---|---|---|
| 2 | B | 100 | A | 46.2 | 1,3 XB | 2 | 16.9 |
| 3 | B | 100 | B | 48.2 | PG | 2 | 16.3 |
| 4 | B | 100 | C | 37.2 | — | — | 19.9 |
| 5 | B | 100 | A | 37.2 | — | — | 19.9 |
| 6 | B | 100 | D | 40.7 | — | — | 19.5 |
| 7 | B | 100 | A | 56.6 | — | — | 17.0 |
| 8 | B | 100 | B | 61.2 | — | — | 16.8 |
| 9 | A | 100 | B | 51.0 | — | — | 17.0 |
| 10 | A | 100 | D | 31.7 | — | — | 19.9 |
| 11 | A | 100 | A | 28.9 | — | — | 19.9 |
| 12 | A | 100 | C | 28.9 | — | — | 20.1 |
| 13 | A | 100 | A | 36.8 | 1,3 XB | 2 | 16.7 |
| 14 | A | 100 | A | 10.2 | 1,3 XB | 4 | 19.9 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a prepolymer containing an allophanate-modified MDI by reacting
   (i) 4,4'-diphenylmethane diisocyanate containing from 2 to 60% by weight of 2,4'-MDI and less than 6% by weight of 2,2'-MDI with
   (ii) an aromatic alcohol containing between 6 and 18 carbon atoms in the presence of
   (iii) an allophanate-forming catalyst in amounts sufficient to produce a prepolymer having an isocyanate group content of from 12 to 32% by weight which prepolymer is stable and liquid at 25° C.
2. The process of claim 1 wherein the aromatic alcohol is selected from the group consisting of phenol, 1-naphthol, 2-naphthol, cresol, bromophenol, chlorophenol, fluorophenol and nitrophenol.
3. The process of claim 1 wherein the allophanate-modified MDI is prepared at 60°-120° C. in the presence of zinc acetylacetonate catalyst.
4. The process of claim 1 wherein benzoyl chloride is used as a stopper for the catalyst.
5. The process as recited in claim 1 further comprising reacting the allophanate-modified MDI with (a) an organic material containing two or more hydroxy, primary amine or secondary amine groups or any combination having a molecular weight of from 400 to 6000 or with (b) a diol having a molecular weight of from 60 to 200 or with a combination of (a) and (b) to produce an allophanate-modified MDI having an isocyanate content of from 5 to 30% by weight.
6. A stable, liquid allophanate-modified MDI which is prepared by the process of claim 1.
7. A stable, liquid allophanate-modified MDI which is prepared by the process of claim 5.

* * * * *